United States Patent [19]

Hochmair et al.

[11] 4,284,856
[45] Aug. 18, 1981

[54] MULTI-FREQUENCY SYSTEM AND METHOD FOR ENHANCING AUDITORY STIMULATION AND THE LIKE

[76] Inventors: Ingeborg J. Hochmair; Erwin S. Hochmair, both of Jaunerstr 27, A-1130, Vienna, Austria

[21] Appl. No.: 77,791

[22] Filed: Sep. 24, 1979

[51] Int. Cl.³ .......................................... H04R 25/02
[52] U.S. Cl. ........................ 179/107 E; 179/107 BC
[58] Field of Search ...................... 179/107 E, 107 BC

[56] References Cited

U.S. PATENT DOCUMENTS

| 3,209,081 | 9/1965 | Ducote et al. | 179/107 BC |
| 3,449,768 | 6/1969 | Doyle | 3/1 |
| 3,752,929 | 8/1973 | Fletcher | 179/1 SA |

FOREIGN PATENT DOCUMENTS

| 1915 | 5/1979 | European Pat. Off. | 179/107 BC |
| 2823798 | 9/1979 | Fed. Rep. of Germany . | |

OTHER PUBLICATIONS

"Multielectrode Intracochlear Implants", Schindler et al., *Arch Otolaryngol*, vol. 103, Dec. 1977, pp. 691–699.
"A Multiple-Electrode Array for Cochlear Implant", Clark et al., *J. Laryngol, Otol*, 90/7, 1976, pp. 623–627.

*Primary Examiner*—Thomas A. Robinson
*Attorney, Agent, or Firm*—Flehr, Hohbach, Test

[57] ABSTRACT

A plurality of carrier signals are modulated by pulses corresponding to signals in audio frequency bands. The carrier signals are transmitted to a receiver having independent channels for receiving and demodulating the transmitted signals. The detected pulses are applied to electrodes on a prosthetic device implanted in the cochlea with the electrodes selectively positioned in the cochlea to stimulate regions having a desired frequency response. The pulses have a frequency which corresponds to the frequency of signals in an audio band and a pulse width which corresponds to the amplitude of signals in the audio band.

22 Claims, 10 Drawing Figures

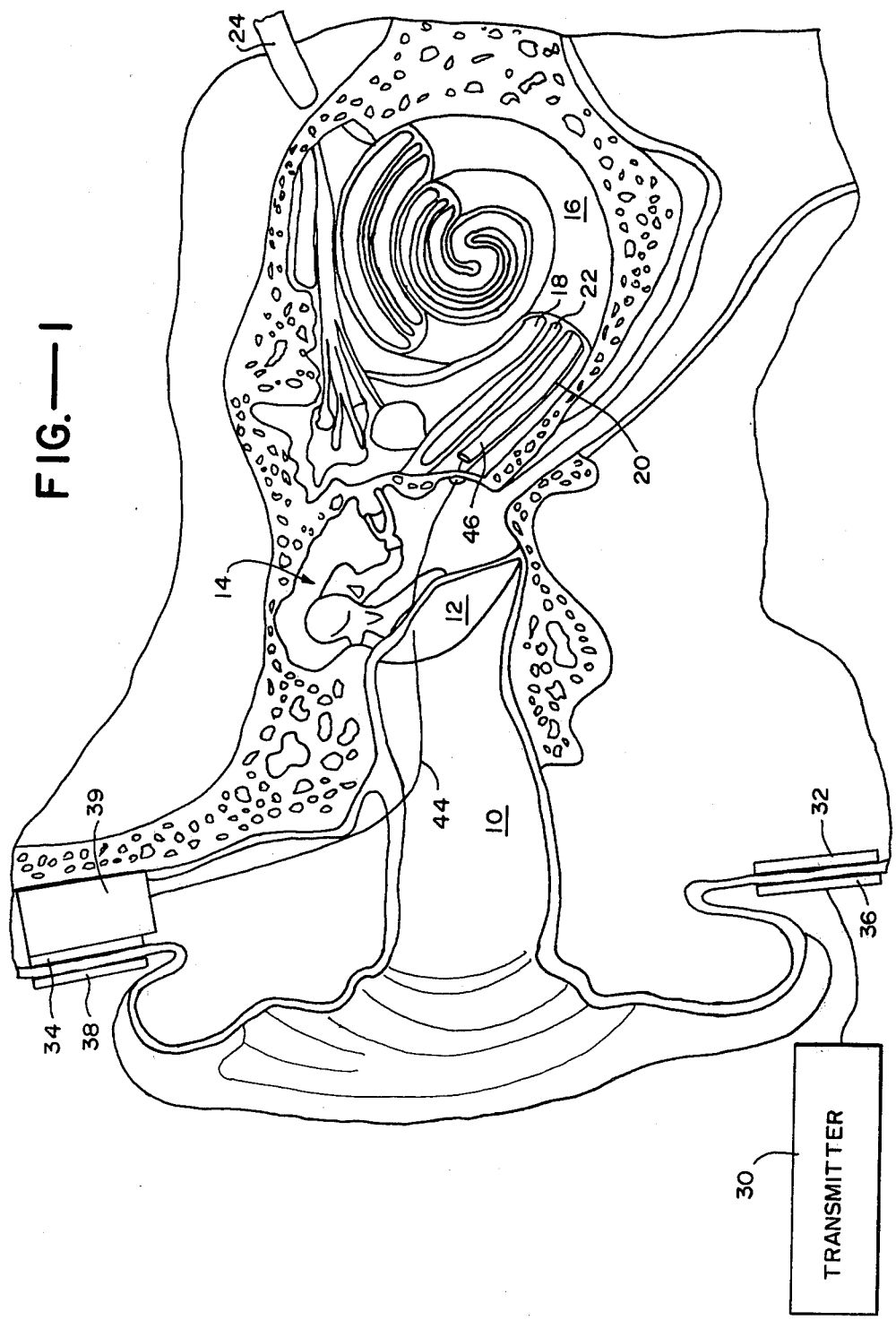
FIG.—1

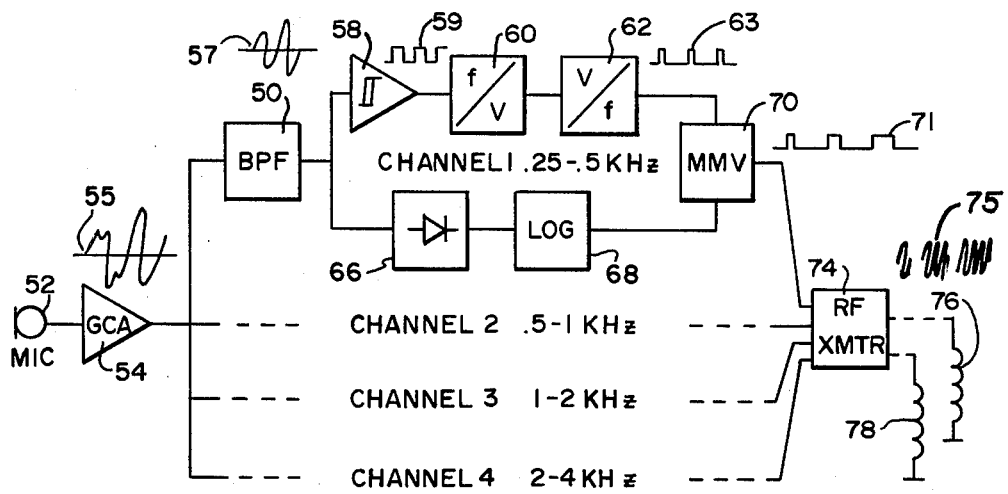
FIG.—2
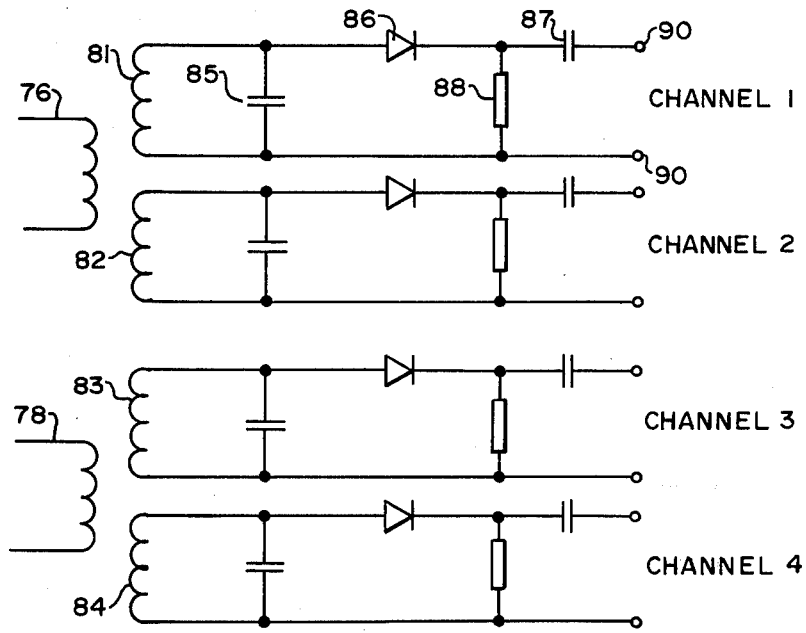
FIG.—3
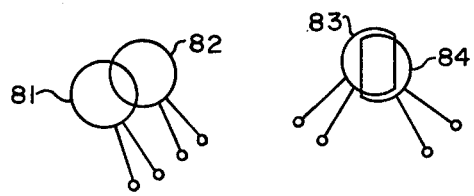
FIG.—4

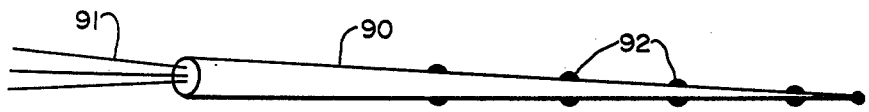
FIG.—5
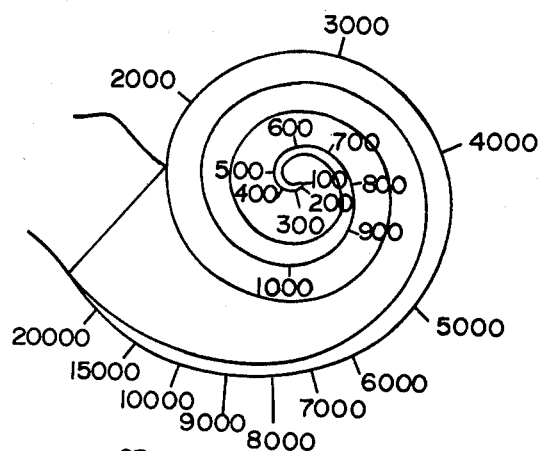
FIG.—6
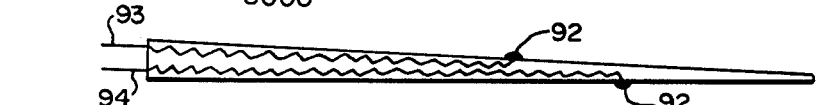
FIG.—7
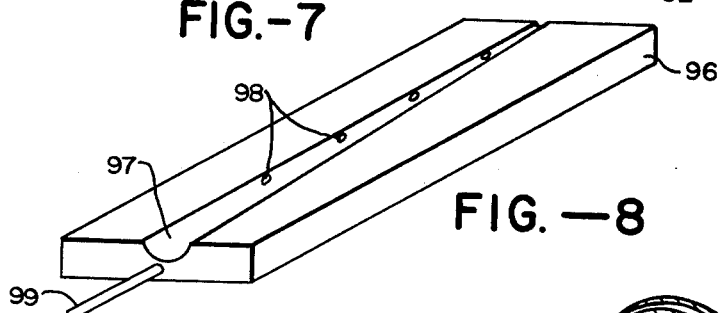
FIG.—8
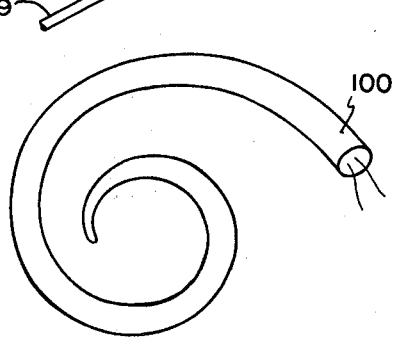
FIG.—9a
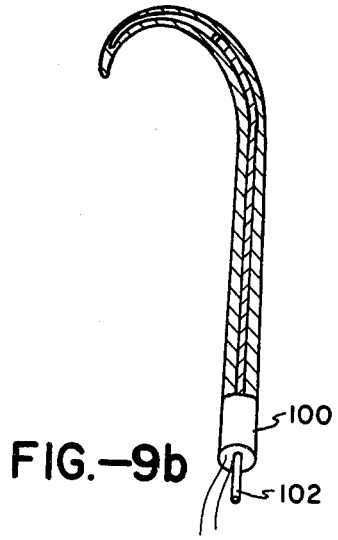
FIG.—9b

MULTI-FREQUENCY SYSTEM AND METHOD FOR ENHANCING AUDITORY STIMULATION AND THE LIKE This invention relates generally to apparatus for neural and muscle stimulation such as for facilitating hearing in the deaf, and more particularly the invention relates to a method and means for stimulating by means of electrical pulses.

The use of subcutaneously implanted hearing devices is known. U.S. Pat. No. 3,209,081 discloses a device which is implanted in the mastoid bone. The receiver makes direct contact with the bone through which sound waves may be conducted to the inner ear.

More recently, implanted prosthetic devices for stimulating the auditory nerve by means of electrical pulses have been disclosed. U.S. Pat. No. 3,449,768 discloses the use of coded pulse trains to create an electrical gradient field to facilitate visual or audio stimulations. U.S. Pat. No. 3,752,929 discloses the use of an electrode including a pair of elongated conductors for implanting in the cochlea.

Schindler et al, "Multielectrode Intracochlear Implants" Arch Otolaryngol, Vol. 103, December 1977, discloses the use of spatial excitation of the cochlear nerve in cats. Clark and Hallworth, "A Multiple-Electrode Array for Cochlear Implant," J. Laryngol, Otol, 90/7, 1976 discloses a ribbon array including a plurality of elongated flat electrodes which are positioned along the length of the cochlea for stimulating the auditory nerve. Similarly, bundles of thin wires have been employed by the Stanford Auditory prosthesis group by direct placement into the auditory nerve.

An object of the present invention is an improved system for neural and muscle stimulation.

Another object of the invention is an improved method of enhancing auditory stimulation by means of multiple electrode stimulation.

Still another object of the invention is electrode means for selectively applying electrical stimulation to the auditory nerve.

Yet another object of the invention is electrode means which is readily inserted into the cochlea.

Another object of the invention is a method of making a multielectrode prosthetic device for cochlear excitation.

A feature of the invention is the transmission of signals corresponding to bands of audio frequencies.

Another feature of the invention is a receiver having independent channels for processing signals corresponding to audio frequency bands.

Still another feature of the invention is electrode means for applying signals corresponding to audio frequency bands to selected regions in the cochlea.

Briefly, in accordance with the invention a multi-frequency system for enhancing audio stimulation, for example, includes a multichannel transmission means for transmitting a plurality of signals each of which is modulated by a signal representing a band of frequencies in the audio range. Multi-channel receiver means for subcutaneous placement is provided for receiving the transmitted signals with each channel of the receiver responsive to one of the transmitted signals representing a band of frequencies. In a preferred embodiment each channel of the receiver is independent and includes a tuned receiving coil for receiving a transmitted signal and detector means for detecting the transmitted modulation signal.

A multi-electrode prosthetic device is provided for cochlea implantation with means connecting a signal from each of the receiver channels to at least one electrode pair of the prosthetic device whereby the prosthetic device provides electrical stimulation to the auditory nerve. Placement of the electrodes in the device is chosen whereby the implanted device will stimulate the cochlea in accordance with the frequency response thereof.

The multi-electrode prosthetic device comprises a molded biocompatible body with a plurality of wires within the body. Each wire is terminated in a contact body such as a ball with the ball positioned at the surface of the body. Advantageously, each wire is wrinkled prior to the molding of the body to provide stress relief and facilitate flexing of the prosthetic device for insertion into the cochlea. The balls at the end of the wires are selectively positioned whereby the inserted prosthetic device stimulates the cochlea in accordance with the frequency response of the cochlea.

In a preferred embodiment, each channel of the transmission means includes a band pass filter for selecting and passing a band of audio frequency signals, a pulse generator, means responsive to the frequency of signals passed by the band pass filter for controlling the frequency of the pulse generator, and means responsive to the amplitude of signals passed by the band pass filter for controlling pulse width in the pulse generator. The output signal from the pulse generator is applied to modulate a carrier frequency in a transmitter.

The signal from the transmission means is transmitted to the receiver by means of a coil connected to the transmitter output. The multi-channel receiver includes a plurality of coils corresponding in number to the number of channels of the receiver, and the transmitter coil and the receiver coils are magnetically coupled. The receiver coils may be provided in spaced apart groups with the coils in each group overlapping to minimize magnetic coupling effects of the receiver coils.

The invention and objects and features thereof will be more readily apparent from the following detailed description and appended claims when taken with the drawings, in which:

FIG. 1 is a section view of a human ear illustrating the application of the present invention.

FIG. 2 is an electrical schematic of a transmitter for use in the multi-frequency system for enhancing audio stimulation in accordance with one embodiment of the present invention.

FIG. 3 is an electrical schematic of one embodiment of a multiple channel receiver for use in a multi-frequency system for enhancing audio stimulation in accordance with the invention.

FIG. 4 is a plan view illustrating the placement of receiver coils in accordance with one embodiment of the invention.

FIG. 5 is a perspective view of one ebodiment of a multi-electrode prosthetic device in accordance with the invention.

FIG. 6 is a schematic of a cochlea illustrating the frequency response thereof.

FIG. 7 is a section view of a multi-electrode prosthetic device in accordance with the invention.

FIG. 8 is a perspective view illustrating a mold useful in fabricating the prosthetic device of FIG. 7.

FIG. 9a is an alternative embodiment of a prosthetic device, and FIG. 9b illustrates the insertion of the device of FIG. 9a.

Referring now to the drawings, FIG. 1 is a section view of a human ear illustrating the application of a multi-frequency audio stimulation system in accordance with the present invention. Normally, sounds are transmitted through the outer ear 10 to the eardrum 12 which moves the bones of the middle ear shown generally at 14 and excites the cochlea shown generally at 16. The cochlea is a long narrow duct wound spirally about its axis for approximately two and one-half turns. The cochlea includes an upper channel 18, the scala vestibuli, and a lower channel 20, scala tympani, with the cochlear duct 22 therebetween. The fluid filled scala vestibuli and scala tympani transmit waves in response to received sounds and in cooperation with the cochlear duct 22 function as a transducer to generate electric pulses which is transmitted to the cochlear nerve 24 and thence to the brain.

In people with total sensorineural hearing loss the cochlea does not respond to sound waves to generate electrical signals which can be transmitted to the cochlear nerve. The multi-frequency stimulation system in accordance with the present invention effects direct electrical stimulation of the cochlea. The system includes a multi-frequency transmitter 30 which may be worn on the body. The transmitter is coupled to an implanted receiver. The coupling is preferably accomplished by means of coils 36 and 38 which are connected to the multi-channel transmitter 30 and coils 32 and 34 associated with the receiver. As will be described hereinbelow in detail, the transmitter 30 transmits a plurality of signals which are modulated in accordance with the signal content of a plurality of audio frequency bands. The transmitted signals are received and detected in the receiver with the detected signal connected through wires 44 to a prosthetic device 46 which is implanted in the cochlea. As will be described further hereinbelow, the prosthetic device includes a plurality of electrodes which are positioned on the surface of the device to provide selective stimulation of the cochlea in accordance with the frequency response thereof.

In a preferred embodiment the multi-frequency system includes four channels corresponding to four frequency bands in the audio frequency range. FIG. 2 is an electrical schematic of an embodiment of the transmitter which includes four channels corresponding to 0.25–0.5 Khz, 0.5–1.0 Khz, 1.0–2.0 Khz, and 2.0–4.0 Khz. The circuitry for each channel is illustrated in block diagram form in channel 1 and includes a band pass filter 50 tuned for the desired frequency band (e.g. 0.25–0.5 Khz for channel 1). Filter 50 receives an audio signal picked up by a microphone 52 and passed through a gain control amplifier 54. The signal from amplifier 54 has a wide frequency range as illustrated at 55, and after passing through the bandpass filter 50 a signal of limited frequency range is provided as shown at 57. Delay circuitry can be included in the lower frequency channels to compensate for the delay normally introduced in transmitting acoustic waves through the length of the cochlea for stimulating the lower frequency stimulation sites near the apex of the cochlea.

The signal 57 is then applied through a limiter 58 which produces a clipped output signal 59 showing the same zero-crossings as wave 57. The clipped wave 59 is applied to a frequency to voltage converter 60 which produces a time varying dc voltage that is proportional to the frequency of signal 59. The frequency to voltage converter comprises suitable circuitry such as a monostable multivibrator which is triggered by signal 59 to generate a plurality of pulses of equal pulse width having a repetition rate at the frequency of the signal 59. The monostable multivibrator output is passed through a low pass filter to generate a time varying dc voltage which is proportional to the pulse rate.

The time varying voltage output from converter 60 is then applied to a voltage to frequency converter 62 such as a voltage controlled oscillator which generates an output signal 63 comprising a train of pulses having a fixed pulse width and a frequency corresponding to the voltage applied to the controlled oscillator. However, the frequency range of the pulse train 63 may vary in a limited range such as 40–400 Hz while the band pass filter passes a smaller or larger frequency range. As will be described further hereinbelow, the auditory nerve can detect signal pitch wherein excitation is limited to electrical pulses at frequency limited to 400 Hz applied to particular stimulation sites in the cochlea. Thus, the passband is transformed into a lower frequency range corresponding to the range of electrical stimulation frequency where pitch discrimination can be achieved. This range is in most cases limited to e.g. 40–400 Hz, although it might also be considerably larger in certain cases.

The signal from bandpass filter 50 is also passed through a rectifier 66 and a logarithmic amplifier 68 which produces a varying dc output voltage which is logarithmically proportional to the amplitude of the rectified signal from rectifier 66.

The signal 63 from converter 62 and the dc voltage from amplifier 68 are applied to a monostable multivibrator 70 which generates an output pulse train 71 with a pulse repetition rate determined by the pulse repetition rate of signal 63 and with a pulse width determined by the voltage from logarithmic amplifier 68. Signal 71 is applied to an RF transmitter 74 for modulating a carrier signal, as illustrated at 75. The modulated carrier is then transmitted by antenna coil 76 or antenna coil 78.

Each of the channels has similar circuitry with the bandpass filters selected to pass the desired frequency band. In each of the channels the monostable multivibrator generates an output pulse train varying in frequency from about 40 to 400 Hz as this frequency range is particularly suitable for stimulating the cochlea. Thus, each channel generates a similar pulse train varying in frequency from 40 to 400 Hz and with varying pulse width, as described, which are used to modulate carrier signals in the transmitter 74. In the illustrated embodiment employing four channels, the RF transmitter includes four carrier signals with two signals being at 12 MHz and two signals being at 31 MHz. The pulse trains from channel 1 and channel 3 are employed to modulate 12 megahertz signals, respectively, and channels 2 and 4 are used to modulate 31 megahertz signals, respectively. The carrier signals modulated by signals 1 and 2 are applied to one output coil and the carrier signals modulated by channel 3 and 4 are applied to a second output coil. Because of the frequency difference in the two carrier frequencies applied to each coil, minimum cross talk results therefrom.

FIG. 3 is an electrical schematic of a multi-channel detector in accordance with a preferred embodiment which includes four independent channels with each channel including a coil 81–84 with coils 81 and 82 magnetically coupled to transmitter coil 76 and the coils 83 and 84 magnetically coupled to the transmitter coil 78. Each of the coils 81-84 is shunted by a capacitor 85 which tunes the coil to 12 megahertz or 31 megahertz, as required for each of channels 1-4. The signal coupled to coil 81 by coil 76 passes through a detector comprising serially connected diode 86 and capacitor 87 and shunt resistor 88. By using pulse modulation and demodulation a Zener diode can be included in parallel with resistor 88 thus limiting the voltage of the detector. Accordingly, effects of voltage variations due to coupling of the transmitter and detector coils can be minimized. The detected voltage across output terminals 90 preferably varies from 0 to 3 volts and at a frequency from 40 to 400 Hz, depending on the detected modulation signal.

Especially for tissue stimulation systems with a small number of independent channels simultaneously carrying different signals, especially 2-9 channels, the following method can be used with advantage.

In order to reduce the space required by the plurality of receiver coils they are arranged in stacked groups. Even though each of the receiver coils is tuned to a different frequency, the mutual coupling of the two or three receiver coils would result in unacceptably high crosstalk, if the coils were just arranged on top of each other. Arranging the coils in such a way to compensate their mutual magnetic flux, their mutual inductance vanishes. Thus two or three independent channels with negligible crosstalk are obtained, using only negligibly more space than one channel. Accordingly, coils 81 and 82 are grouped together and spaced from coils 83 and 84, as illustrated in the plan view thereof in FIG. 4. Each of the coils has a diameter on the order of 1.5 to 2 centimeters and the spacing between the two groups of coils is approximately 3 centimeters to prevent crosstalk between the groups. As illustrated, coils 81 and 82 and coils 83 and 84 are overlapped to minimize crosstalk between the coils in each group. The overlapping of the coils provides offsetting flux from one coil to the other thereby minimizing distortion or crosstalk between the two coils. Since coils 81 and 82 are tuned to different frequencies (e.g. 12 MHz and 31 MHz, respectively), each channel of the receiver receives and detects only the signal from the transmission coil to which it is coupled.

The detected signals in each of the receiver channels are connected to a multi-electrode prosthetic device such as the device 90 illustrated in FIG. 5. Each channel can be connected to one or more electrodes having contacts positioned on the prosthetic device to stimulate a region of the cochlea for a desired frequency response. Thus, bipolar stimulation, unipolar stimulation against a remote ground, or a common distributed ground stimulation can be employed. The device comprises an elongated molded body of a silicone elastomer such as Silastic in which a plurality of wires shown generally at 91 are implanted. Each wire is terminated in a ball 92 which is positioned at the surface of the device 90. The spacing of the balls on the surface of the device 90 provides selected frequency response when the device is inserted into the cochlea. As noted in the schematic of a cochlea shown in FIG. 6, the frequency response generated by the cochlea varies from a high frequency at the basal turn of the cochlea and has a progressingly lower frequency response towards the apex of the cochlea. Accordingly, by proper positioning the electrode contacts or balls 92 within the cochlea, the electrical stimulation of the cochlea provided by the prosthetic device will induce a desired frequency response. By the additional variation of stimulation frequency a pitch continuum can be achieved.

FIG. 7 is a section view of the prosthetic device of FIG. 5 illustrating the positioning of wires 93 and 94 within the device. To facilitate illustration only two wires are shown. Each of the wires is wrinkled to provide stress relief and to facilitate flexing of the prosthetic device as it is inserted into the cochlea. In a preferred embodiment the wires are Teflon coated platinum (90%)-iridium (10%) wires having a diameter of 25 microns. The balls at the ends of the wire are 300 microns in diameter and are formed by heating the wires in a flame until the wire tips melt. The balls are arranged in pairs in two diametrically opposed rows. In one embodiment the total diameter of the prosthetic device is 0.9 millimeter and is tapered to about 0.5 millimeter at its tip. Overall length must accommodate an insertion in the cochlea of 20-25 millimeters.

FIG. 8 is a perspective view of the bottom portion 96 of a suitable mold for forming the prosthetic device and includes a centrally disposed tapered channel 97 of the desired device configuration. A plurality of holes 98 are provided in the surface of channel 97 with each of the holes 98 in communication through body 96 with a vacuum line 99. In forming the prosthetic device, the wires are first positioned in the mold cavity with the spherical end portions of the wires placed in holes 98 and maintained in position by means of the vacuum applied to line 99. The mold is then assembled and the cavity defined by channel 97 is filled with Silastic material. The vacuum chuck provided by holes 98 ensures proper positioning of the ball contacts on the surface of the prosthetic device to provide the desired frequency stimulation by the device when inserted into the cochlea.

FIG. 9a is a perspective view of an alternative embodiment 100 of prosthetic device which is molded to conform to the shape of the cochlea. Insertion of the device in the cochlea is illustrated in the section view in FIG. 9b in which a straight rod 102 such as steel wire is inserted into the molded body 100. The rod 100 is slowly extracted therefrom as the device is inserted into the cochlea whereby the body 100 reassumes its molded configuration.

The method of auditory stimulation utilizing the multi-frequency system in accordance with the present invention provides improved hearing in the deaf and hard of hearing. The use of frequency band signals enhances the perceived sound and the selective stimulation of the cochlea enhances the auditory response. Since the receiver comprises passive devices, no power supply other than the transmitted signals is required. The prosthetic device is readily manufactured with exact electrode positioning to achieve desired frequency response when stimulating the cochlea. While pulse modulation is employed in the preferred embodiment, other modulations such as amplitude or frequency can be employed. Analog signals can be employed as well as pulsed or digital signals in practicing the invention. While in the described embodiment the audio frequency bands are transformed to corresponding signals having frequencies of 40-400 Hz, the corresponding signals can have the same frequencies as the audio bands or the frequencies may be unrelated.

Thus, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A multi-frequency system for electrical stimulation comprising:

transmission means for transmitting a plurality of signals each of which is modulated by a signal representing a band of frequencies, said transmission means including at least one coil for transmitting said plurality of modulated signals, passive multi-channel receiver means for receiving said transmitted signals with each channel responsive to one of said signals representing a band of frequencies, said multi-channel receiver means including a plurality of coils corresponding in number to the number of channels in said receiver means, a multi-electrode prosthetic device, and means connecting a signal from each of said channels to at least one electrode of said prosthetic device whereby said prosthetic device provides electrical stimulation.

2. A multi-frequency system as defined by claim 1 wherein said system provides auditory stimulation and said band of frequencies are in the audio band and said prosthetic device is implanted in the cochlea.

3. A multi-frequency system as defined by claim 1 wherein said multi-channel receiver means comprises independent channels for processing said transmitted signals.

4. A multi-frequency system as defined by claim 2 wherein each independent channel comprises a tuned receiving coil and a signal detector.

5. A multi-frequency system as defined by claim 2 wherein said multi-electrode prosthetic device comprises an elongated molded biocompatible body, a plurality of wires within said body, each wire terminating in a contact with the contact positioned at the surface of said body.

6. A multi-frequency system as defined by claim 5 wherein each wire is wrinkled prior to molding to facilitate flexing of said body upon insertion into the cochlea.

7. A multi-frequency system as defined by claim 5 wherein said contacts are selectively positioned to stimulate the cochlea in accordance with the frequency response of the cochlea.

8. A multi-frequency system as defined by claim 2 wherein said transmission means includes a plurality of channels corresponding to the plurality of bands of frequencies in the audio range, each channel including a band pass filter for selecting a band of audio frequency signals, a pulse generator, means connected to said filter and responsive to frequencies of signals from said band pass filter for controlling the frequency of said pulse generator, means responsive to amplitude of signals passed by said band pass filter for controlling pulses of said pulse generator, and a transmitter for modulating a carrier signal by the signal from said pulse generator.

9. A multi-frequency system as defined by claim 8 wherein said pulse generator is a monostable multivibrator and said means responsive to amplitude of signals controls pulse width.

10. A multi-frequency system as defined by claim 8 wherein said plurality of channels correspond to the frequencies of 0.25–0.5 KHz, 0.5–1.0 KHz, 1.0–2.0 KHz, and 2.0–4.0 KHz.

11. A multi-frequency system as defined by claim 8 wherein said multichannel receiver means includes four channels with each channel including a coil, said transmitter means including two coils with each coil receiving two modulated carrier signals, a first two of said receiver coils being magnetically coupled to one of said transmitter coils, and the other two of said receiver coils being magnetically coupled to the other of said transmitter coils.

12. A multi-frequency system as defined by claim 11 wherein said first two receiver coils are overlapping and the other two receiver coils are overlapping to minimize mutual magnetic coupling of said coils.

13. A multi-channel receiver for subcutaneous placement comprising a plurality of independent channels, each channel including a coil tuned to receive a transmitted signal, a detector interconnected with the coil to detect a modulation signal, and means for connecting the detected modulation signal to electrode stimulation means.

14. A multi-channel receiver as defined by claim 13 wherein said coils are provided in spaced apart groups with the coils in each group overlapping to minimize mutual magnetic coupling effects of the coils.

15. A multi-channel receiver as defined by claim 13 and further including a multi-electrode prosthetic device for cochlea implantation.

16. A multi-channel receiver as defined by claim 15 wherein said prosthetic device comprises an elongated molded biocompatible body, a plurality of wires within said body, each wire terminating in a contact with the contact positioned at the surface of said body.

17. A multi-channel receiver as defined by claim 16 wherein said contacts are selectively positioned on the surface of said body to stimulate the cochlea in accordance with the frequency response of the cochlea.

18. A multi-electrode prosthetic device for cochlea implantation comprising an elongated molded body of biocompatible material, a plurality of wires within said body, each wire terminating in a contact with the contact positioned at the surface of said body, said wires being wrinkled to provide stress relief and facilitate flexing of said device.

19. A multi-electrode prosthetic device for cochlea implantation as defined by claim 18 wherein said contacts are selectively positioned in said body to stimulate the cochlea in accordance with the frequency response of the cochlea.

20. A method of fabricating a multi-electrode prosthetic device having a molded elongated body, a plurality of wires within said body, each wire terminating in a ball with the ball positioned at the surface of said body, the method including the steps of (a) providing a plurality of wires with contacts formed on one end thereof, (b) wrinkling said wires whereby flexibility of the body is facilitated, (c) placing said wires in a mold with said contacts maintained in position by vacuum chuck means, and (d) filling said mold with biocompatible material.

21. The method of enhancing auditory stimulation comprising the steps of transmitting a plurality of modulated signals with each signal being modulated by pulses having a frequency determined by the frequencies of signals in a frequency band and having a pulse width corresponding to the amplitude of signals in a frequency band, receiving said plurality of modulated signals, detecting the modulation signals of said modulated signals, and applying each detected signal to electrode means implanted in a cochlea.

22. The method as defined by claim 21 wherein said step of applying said detected signals includes connecting each detected signal to electrode means located in the cochlea at a position having a frequency response corresponding to the frequency band of the modulated signal.

* * * * *